(12) United States Patent
Blackler et al.

(10) Patent No.: US 6,815,457 B1
(45) Date of Patent: Nov. 9, 2004

(54) THIAZOLIDINEDIONE DERIVATIVE AND ITS USE AS ANTIDIABETIC

(75) Inventors: Paul David James Blackler, Cadiz (ES); Robert Gordon Giles, Tonbridge (GB); Michael Sasse, Tonbridge (GB)

(73) Assignee: SmithKline Beecham p.l.c., Brentford (GB)

( * ) Notice: Subject to any disclaimer, the term of this patent is extended or adjusted under 35 U.S.C. 154(b) by 0 days.

(21) Appl. No.: 10/030,323

(22) PCT Filed: Apr. 19, 2000

(86) PCT No.: PCT/GB00/01514

§ 371 (c)(1),
(2), (4) Date: May 15, 2002

(87) PCT Pub. No.: WO00/64892

PCT Pub. Date: Nov. 2, 2000

(30) Foreign Application Priority Data

Apr. 23, 1999 (GB) .............................................. 9909472
May 25, 1999 (GB) .............................................. 9912197

(51) Int. Cl.[7] ................... C07D 417/12; A61K 31/425; A61K 31/44

(52) U.S. Cl. .................................... 514/342; 546/269.7

(58) Field of Search ........................ 546/269.7; 514/342

(56) References Cited

U.S. PATENT DOCUMENTS

| | | | | |
|---|---|---|---|---|
| 5,002,953 | A | 3/1991 | Hindley ...................... | 514/275 |
| 5,478,852 | A | * 12/1995 | Olefsky et al. ............. | 514/342 |
| 5,741,803 | A | 4/1998 | Pool et al. .................. | 514/342 |
| 5,910,592 | A | 6/1999 | Pool et al. ............... | 546/269.7 |
| 6,288,095 | B1 | 9/2001 | Hindley ...................... | 514/367 |
| 2002/0133016 | A1 | 9/2002 | Lynch et al. ............. | 546/269.7 |
| 2002/0137940 | A1 | 9/2002 | Sasse et al. ............... | 546/269.7 |

FOREIGN PATENT DOCUMENTS

| | | | |
|---|---|---|---|
| EP | 0 306 228 B1 | 11/1999 | |
| WO | WO 93/10254 | 3/1993 | |
| WO | WO 94/05659 | 3/1994 | |
| WO | WO 95/21603 | 8/1995 | |
| WO | WO 95/21608 | 8/1995 | |
| WO | WO 99/31093 | 6/1999 | |
| WO | WO 99/31094 | 6/1999 | ......... C07D/417/12 |
| WO | WO 99/31095 | 6/1999 | |
| WO | WO 00/64892 | 11/2000 | |
| WO | WO 00/64893 | 11/2000 | |
| WO | WO 00/64896 | 11/2000 | |
| WO | WO 02/26737 | 4/2002 | |

OTHER PUBLICATIONS

Cantello, et al., "The Synthesis of BRL 49653—A Novel and Potent Antihyperglycaemic Agent", *Bioorganic & Medicinal Chemistry Letters*, 4(10): 1181–1184 (1994).

Haleblian, et al., "Pharmaceutical Applications of Polymorphism", *Journal of Pharmaceutical Sciences*, 58(8): 911–929 (1969).

J. Haleblian and W. McCrone, "Pharmaceutical Applications of Polymorphism", *Journal of Pharmaceutical Sciences*, vol. 58, No. 8, pp. 911–929 (1969).

* cited by examiner

*Primary Examiner*—Zinna Northington Davis
(74) *Attorney, Agent, or Firm*—Kathyrn L. Sieburth; Mary E. McCarthy; Charles M. Kinzig

(57) ABSTRACT

A polymorphic form of 5-[4-[2-(N-methyl-N-(2-pyridyl) amino)ethoxy]-benzyl]thiazolidine-2,4-dione, maleic acid salt (the "Polymorph") characterized in that it: (i) provides an infra red spectrum containing peaks at 1360, 1326, 1241, 714 and 669 cm$^{-1}$; and/or (ii) provides a Raman spectrum containing peaks at 1581, 768, 670, 271 and 226 cm$^{-1}$; and/or (iii) provides a solid-state nuclear magnetic resonance spectrum containing peaks at chemical shifts substantially as set out in Table I; and/or (iv) provides an X-ray powder diffraction (XRPD) pattern containing peaks substantially as set out in Table II; a process for preparing such a compound, a pharmaceutical composition containing such a compound and the use of such a compound in medicine.

41 Claims, 4 Drawing Sheets

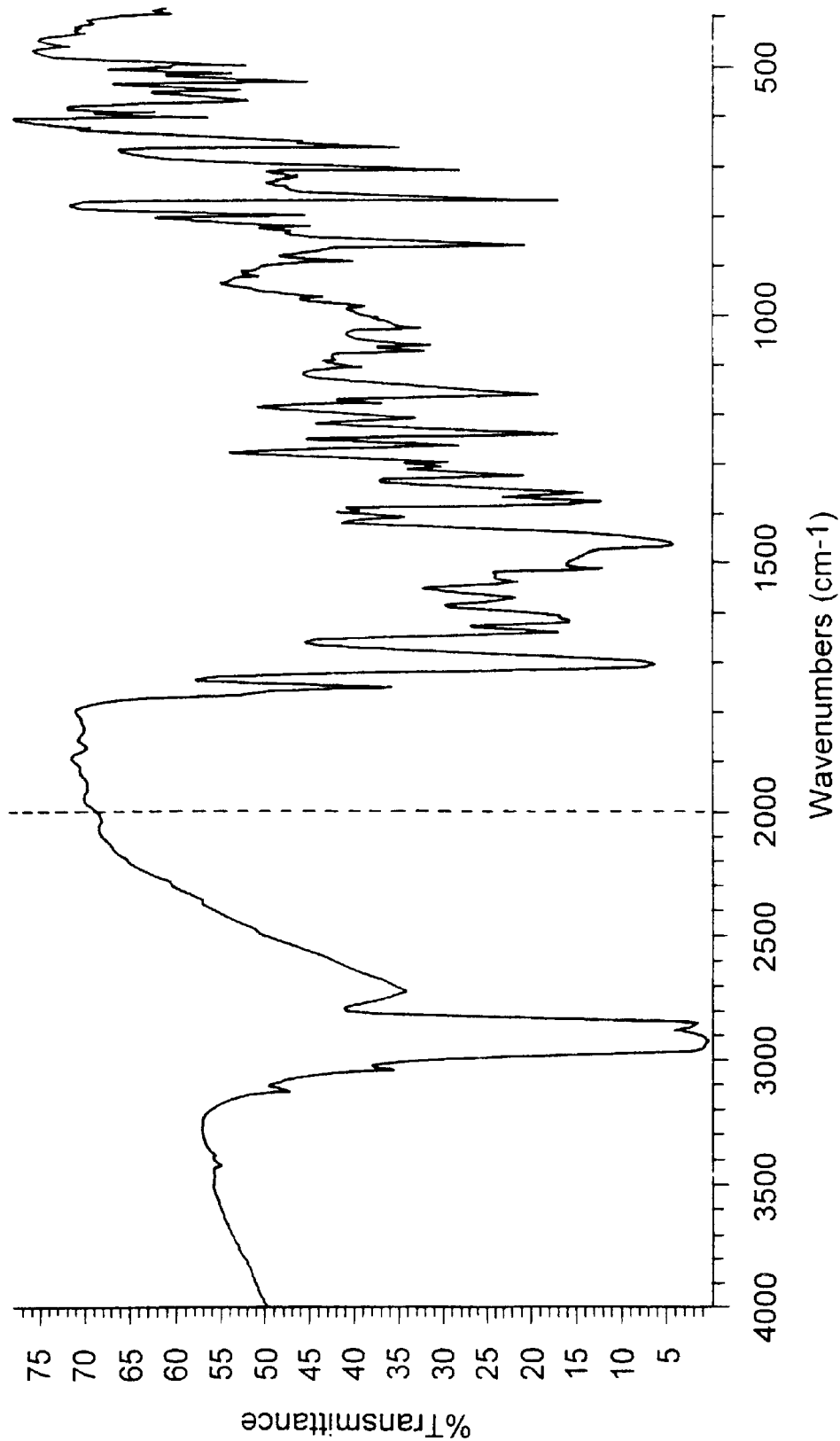
Fig. 1 Infrared Spectrum of the Polymorph

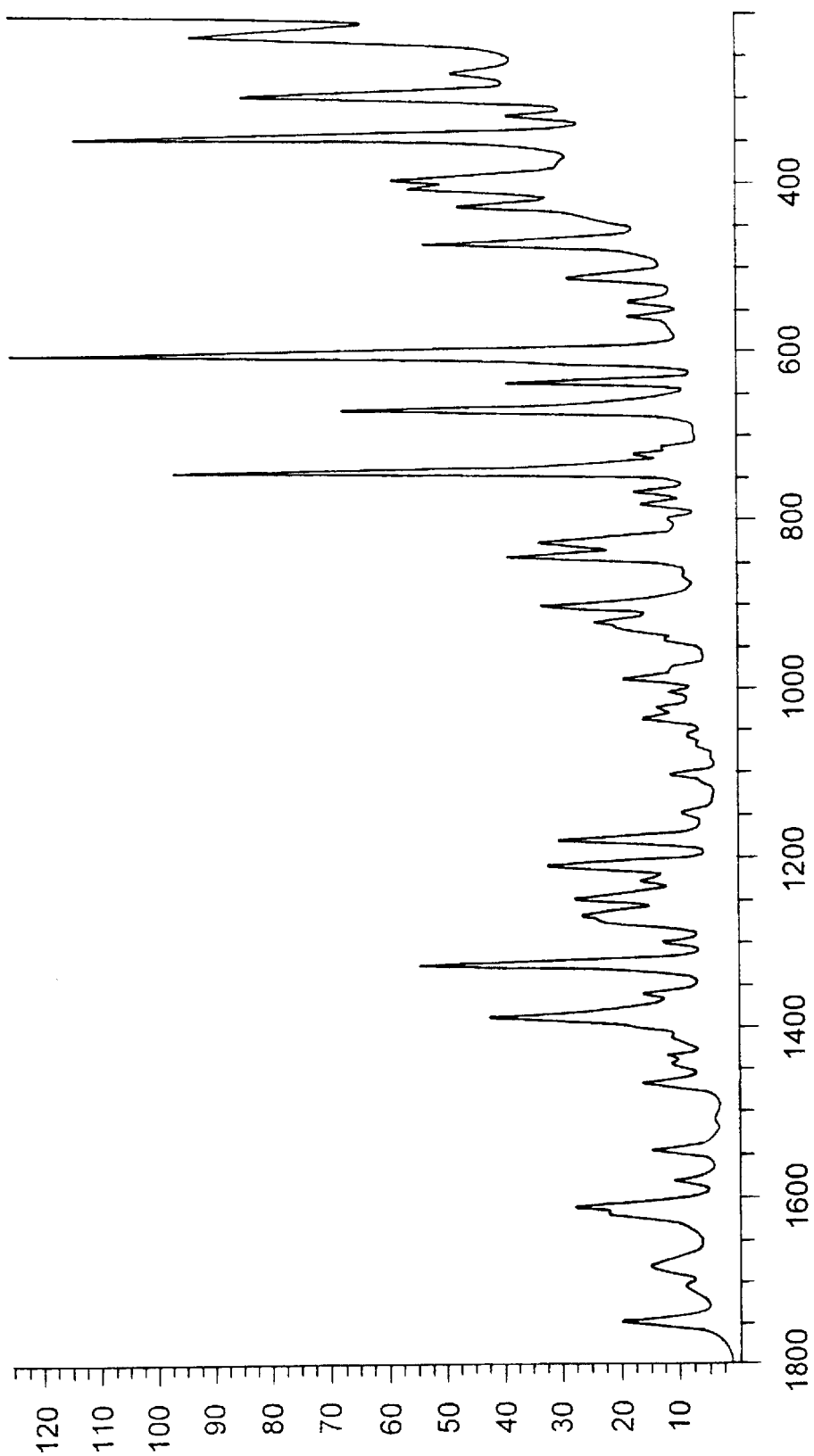
Fig. 2 Raman Spectrum of the Polymorph

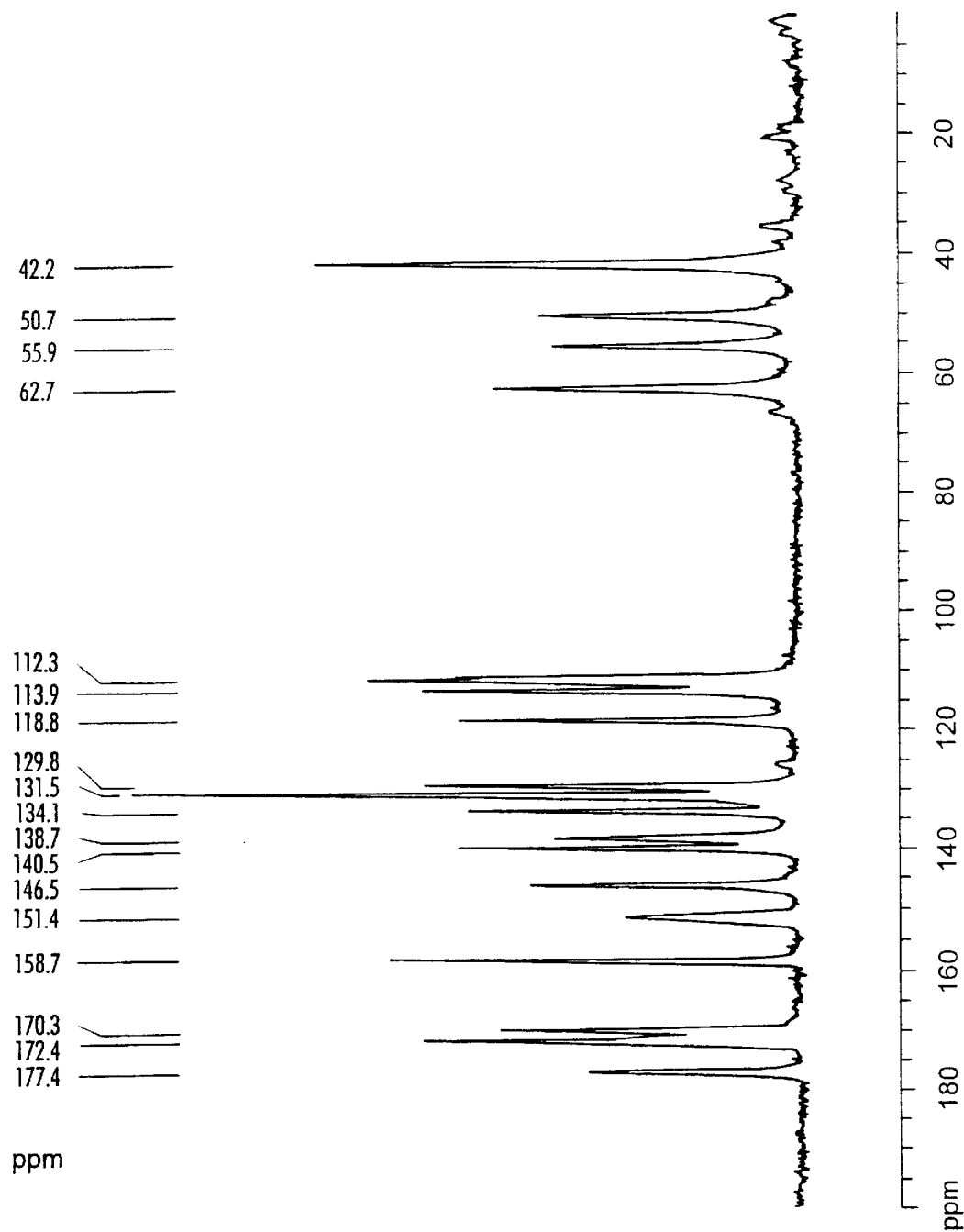
Fig. 3 Solid-State NMR Spectrum of the Polymorph

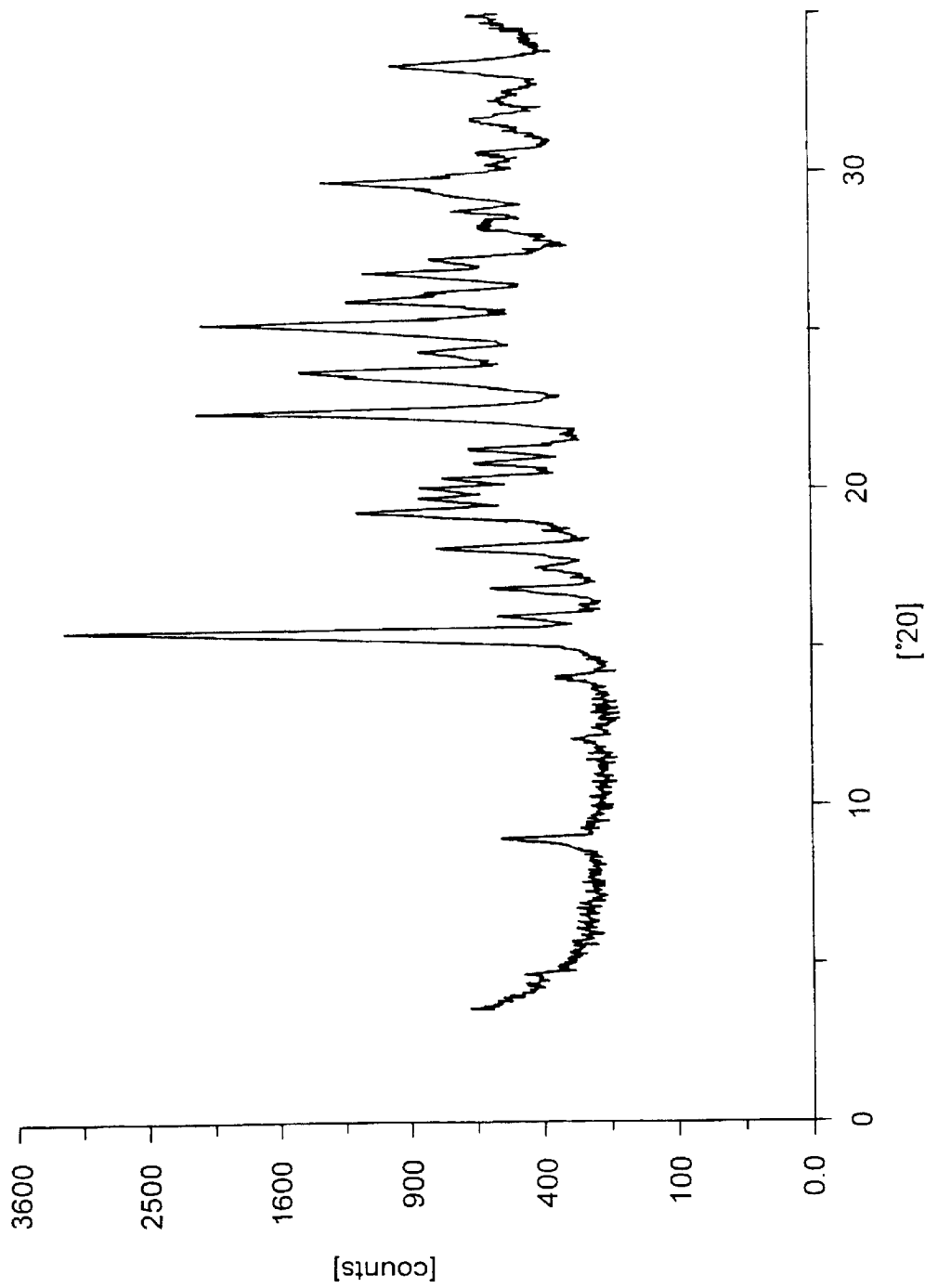

THIAZOLIDINEDIONE DERIVATIVE AND ITS USE AS ANTIDIABETIC

This invention relates a novel pharmaceutical, to a process for the preparation of the pharmaceutical and to the use of the pharmaceutical in medicine.

International Patent Application, Publication Number WO94/05659 discloses certain thiazolidinedione derivatives having hypoglycaemic and hypolipidaemic activity including 5-[4-[2-(N-methyl-N-(2-pyridyl)amino)ethoxy]benzyl]thiazolidine-2,4-dione, maleic acid salt (hereinafter also referred to as "Compound (I)").

International Patent Applications, Publication Numbers WO99/31093, WO99/31094 and WO99/31095 each disclose distinct hydrates of Compound (I).

It has now been discovered that Compound (I) exists in a novel polymorphic form which is particularly suitable for bulk preparation and handling. The novel form can be prepared by an efficient, economic and reproducible process particularly suited to large-scale preparation.

The novel polymorphic form ('the Polymorph') also has useful pharmaceutical properties and in particular it is indicated to be useful for the treatment and/or prophylaxis of diabetes mellitus, conditions associated with diabetes mellitus and certain complications thereof.

Accordingly, the present invention provides a polymorphic form of 5-[4-[2-(N-methyl-N-(2-pyridyl)amino)ethoxy]benzyl]thiazolidine-2,4-dione, maleic acid salt characterised in that it:

(i) provides an infra red spectrum containing peaks at 1360, 1326, 1241, 714 and 669 cm$^{-1}$; and/or (ii) provides a Raman spectrum containing peaks at 1581, 768, 670, 271 and 226 cm$^{-1}$; and/or (iii) provides a solid-state nuclear magnetic resonance spectrum containing peaks at chemical shifts substantially as set out in Table I; and/or (iv) provides an X-ray powder diffraction (XRPD) pattern containing peaks substantially as set out in Table II.

In one favoured aspect, the Polymorph provides an infrared spectrum substantially in accordance with FIG. I.

In one favoured aspect, the Polymorph provides a Raman spectrum substantially in accordance with FIG. II.

In one favoured aspect, the Polymorph provides a solid-state nuclear magnetic resonance spectrum substantially in accordance with FIG. III.

In one favoured aspect, the Polymorph provides an X-ray powder diffraction (XRPD) pattern substantially in accordance with FIG. IV.

The present invention encompasses the Polymorph isolated in pure form or when admixed with other materials, for example the known forms of Compound I or any other material.

Thus in one aspect there is provided the Polymorph in isolated form.

In a further aspect there is provided the Polymorph in pure form.

In yet a further aspect there is provided the Polymorph in crystalline form.

The invention also provides a process for preparing the Polymorph, characterised in that a slurry of Compound (I) in aqueous ethanol containing up to about 2.5% w/v water, preferably aqueous denatured ethanol containing up to about 2.5% w/v water, for example 2.5% w/v water, is heated, suitably to a temperature in the range of from 35° C. and 60° C., such as 40° C. to 50° C., for example 45° C., for an extended period of time, for example 65 hours, after which time the Polymorph is recovered from the denatured ethanol. Optionally, the reaction mixture is seeded with the Polymorph.

In a further process of the invention, Compound (I) is admixed with denatured ethanol, heated to an elevated temperature, preferably a temperature in the range of from 35° C. and 60° C., such as 40° C. to 50° C., for example from 45° to 47° C., over an extended period of time, for example 65 hours, after which time the Polymorph is recovered from the solvent. Optionally, the reaction mixture is seeded with Polymorph.

In a further process a solution of Compound (I) in denatured ethanol containing up to 2.5% w/v water, for example 0.8 to 2.5% w/v water, at 55° C. is seeded with the Polymorph then cooled to a temperature in the range of from 20° C. to 25° C. to provide the Polymorph. The Polymorph is then recovered from the denatured ethanol.

The solution of Compound (I) in the denatured ethanol is conveniently prepared by dissolving Compound (I) in the required amount of denatured ethanol at an elevated temperature, for example 60° C. In our hands this latter process is also effectively carried out using Compound (I) containing up to 25% w/w of the hydrate disclosed in WO99/31093 mentioned above Conveniently the Polymorph is recovered from the reaction solvent, such as denatured ethanol, by filtration and subsequent drying, preferably at an elevated temperature, for example 45° C.

In a further aspect the present invention also provides a process for preparing Compound (I) (also for convenience referred to as the "Original Polymorph") from the Polymorph of the invention, which process comprises first preparing a solution of the Polymorph in a mixture (100:1 v/v) of absolute ethanol and methanol, at an elevated temperature, suitably in the range of from 60° C. to 75° C. for example at 68° C., and then allowing the solution to cool to ambient temperature, for example 20–25° C., thereby allowing the Original Polymorph to crystallise.

In a preferred form of the said process to prepare the Original Polymorph, the solution of the Polymorph in the absolute ethanol/methanol mixture is filtered, usually once complete dissolution of the Polymorph is attained and the resulting solution is reheated to an elevated temperature, for example to 65° C., which solution is then allowed to cool to ambient temperature, for example 20 to 25° C.

In the above mentioned processes for preparing the Original Polymorph the solution may be seeded with the Original Polymorph but this is not essential.

Compound (I) is prepared according to known procedures, such as those disclosed in WO94/05659. The disclosures of WO94/05659 are incorporated herein by reference.

For the avoidance of doubt the term "Compound (I)" as used herein refers to the form of 5-[4-[2-(N-methyl-N-(2-pyridyl)amino)ethoxy]benzyl]thiazolidine-2,4-dione, maleic acid salt as disclosed an characterised in International Patent Application, Publication Number WO94/05659.

When used herein "denatured ethanol" means ethanol containing small amounts of methanol, usually up to 5% v/v of methanol, such as from 0.9% v/v to 5% v/v of methanol, for example ethanol containing 4%v/v of methanol.

When used herein the term 'prophylaxis of conditions associated with diabetes mellitus' includes the treatment of conditions such as insulin resistance, impaired glucose tolerance, hyperinsulinaemia and gestational diabetes.

Diabetes mellitus preferably means Type II diabetes mellitus.

Conditions associated with diabetes include hyperglycaemia and insulin resistance and obesity. Further conditions associated with diabetes include hypertension, cardiovascular disease, especially atherosclerosis, certain eating disorders, in particular the regulation of appetite and food intake in subjects suffering from disorders associated with under-eating, such as anorexia nervosa, and disorders associated with over-eating, such as obesity and anorexia bulimia. Additional conditions associated with diabetes include polycystic ovarian syndrome and steroid induced insulin resistance.

The complications of conditions associated with diabetes mellitus encompassed herein includes renal disease, especially renal disease associated with the development of Type II diabetes including diabetic nephropathy, glomerulonephritis, glomerular sclerosis, nephrotic syndrome, hypertensive nephrosclerosis and end stage renal disease.

As mentioned above the compound of the invention has useful therapeutic properties: The present invention accordingly the Polymorph for use as an active therapeutic substance.

More particularly, the present invention provides the Polymorph for use in the treatment and/or prophylaxis of diabetes mellitus, conditions associated with diabetes mellitus and certain complications thereof.

The Polymorph may be administered per se or, preferably, as a pharmaceutical composition also comprising a pharmaceutically acceptable carrier. The formulation of the Polymorph and dosages thereof are generally as disclosed for Compound (I) in International Patent Application, Publication Numbers WO94/05659 and WO98/55 122.

Accordingly, the present invention also provides a pharmaceutical composition comprising the Polymorph and a pharmaceutically acceptable carrier therefor.

The Polymorph is normally administered in unit dosage form.

The active compound may be administered by any suitable route but usually by the oral or parenteral routes. For such use, the compound will normally be employed in the form of a pharmaceutical composition in association with a pharmaceutical carrier, diluent and/or excipient, although the exact form of the composition will naturally depend on the mode of administration.

Compositions are prepared by admixture and are suitably adapted for oral, parenteral or topical administration, and as such may be in the form of tablets, capsules, oral liquid preparations, powders, granules, lozenges, pastilles, reconstitutable powders, injectable and infusable solutions or suspensions, suppositories and transdermal devices. Orally administrable compositions are preferred, in particular shaped oral compositions, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art.

Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate.

Solid oral compositions may be prepared by conventional methods of blending, filling, tabletting or the like. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the active compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the active compound is suspended in the vehicle instead of being dissolved and sterilised by exposure to ethylene oxide before suspending in the sterile vehicle. Advantageously, a surfactant or wetting agent is included in the composition to facilitate uniform distribution of the active compound.

In addition such compositions may contain further active agents such as anti-hypertensive agents and diuretics.

In addition, the Polymorph may be used in combination with other antidiabetic agents such as insulin secretagogues, for example sulphonylureas, biguanides, such as metformin, alpha glucosidase inhibitors, such as acarbose, beta agonists, and insulin such as those disclosed in WO98/57649, WO98/57634, WO98/57635 or WO98/57636. The other antidiabetic agents, the amounts thereof and methods of administration are as described in the above mentioned publications. The formulation of the Polymorph and dosages thereof in said combinations are generally as disclosed for Compound (I) in the above mentioned publications. As is common practice, the compositions will usually be accompanied by written or printed directions for use in the medical treatment concerned.

As used herein the term 'pharmaceutically acceptable' embraces compounds, compositions and ingredients for both human and veterinary use: for example the term 'pharmaceutically acceptable salt' embraces a veterinarily acceptable salt.

The present invention further provides a method for the treatment and/or prophylaxis of diabetes mellitus, conditions associated with diabetes mellitus and certain complications thereof, in a human or non-human mammal which comprises administering an effective, non-toxic, amount of the Polymorph to a human or non-human mammal in need thereof.

Conveniently, the active ingredient may be administered as a pharmaceutical composition herein before defined, and this forms a particular aspect of the present invention.

In the treatment and/or prophylaxis of diabetes mellitus, conditions associated with diabetes mellitus and certain complications thereof the Polymorph may be taken in doses, such as those described above.

Similar dosage regimens are suitable for the treatment and/or prophylaxis of non-human mammals.

In a further aspect the present invention provides the use of the Polymorph for the manufacture of a medicament for the treatment and/or prophylaxis of diabetes mellitus, conditions associated with diabetes mellitus and certain complications thereof.

No adverse toxicological effects are indicated in the above mentioned treatments for the compounds of the invention.

The following examples illustrate the invention but do not limit it in any way.

EXAMPLES

Example 1

A slurry of Compound (1) (3.0 g, prepared as per WO94/05659 in denatured ethanol (30.5 ml, water content 2.5% w/v)) was heated at 45° C. for 65 hours. The product was filtered at 45° C. and dried at 50° C. in vacuo to give the Polymorph (1.55 g).

Example 2

To a mixture of absolute ethanol (30 ml, water <0.1% w/v) and methanol (1.2 ml) was added Compound (I) (2.00 g). The resulting suspension was heated to 45–7° C. and maintained at this temperature for 65 h. The solid was isolated at 45° C. and dried at 50° C. in vacuo to give 0.83 g (41%) of Polyrnorph.

Example 3

Compound (I) (6.0 g, containing approximately 25% w/w of the hydrate disclosed in WO99/31093) was heated at 60° C. in denatured ethanol (60 ml, water content 0.8% w/v) until complete dissolution was obtained. The resultant solution was cooled to 55° C., seeded with the title compound (0.06 g), then cooled to 20-25° C. The product was filtered, washed with denatured ethanol (10 ml) and dried at 50° C. in vacuo to give the Polymorph (4.8 g, 80%).

Example 4

Conversion of the Polymonph to Compound (I) (the Original Polymorph)

The Polymorph (4.0 g) was heated to 68° C. in a mixture of absolute ethanol (40 ml) and methanol (0.4 ml) until complete dissolution was obtained. The resultant solution was filtered, re-heated to 65° C., and then cooled to 20–25° C. The product was filtered, washed with absolute ethanol (8 ml) and dried at 50° C. in vacuo to give Compound (1) as disclosed in WO94/05659 (3.32 g, 83%).

CHARACTERISING DATA: The following characterising data were generated for The polymorph:

A Water Content

This was determined as 0.08% w/w using a Karl Fischer apparatus.

B Infrared

The infrared absorption spectrum of a mineral oil dispersion of the Polymorph was obtained using a Nicolet 710 FT-IR spectrometer at 2 cm$^{-1}$ resolution. Data were digitised at 1 cm$^{-1}$ intervals. The spectrum obtained is shown in FIG. I. Peak positions are as follows: 2720, 1750, 1703, 1640, 1618, 1610, 1573, 1541, 1529, 1513, 1412, 1400, 1360, 1326, 1309, 1300, 1265, 1241, 1213, 1183, 1162, 1112, 1096, 1080, 1068, 1033, 1014, 989, 972, 933, 902, 866, 843, 832, 812, 774, 741, 734, 729, 669, 660, 636, 613, 605, 577, 558, 540, 527, 515, 508 and 473 cm$^{-1}$.

C Raman

The Raman spectrum of the Polymorph was recorded through a glass vial using a Perkin Elmer 2000R spectrometer at 4 cm$^{-1}$ resolution and is shown in FIG. II (X-axis shows Intensity, Y-axis shows Raman shift cm$^{-1}$, 1800–200 cm$^{-1}$). Excitation was achieved using a Nd:YAG laser (1064 nm) with a power output of 400 mW. Peak positions areas follows: 1749, 1706, 1683, 1611, 1581, 1546, 1511, 1468, 1445, 1435, 1388, 1361, 1327, 1301, 1269, 1250, 1229, 1210, 1179, 1149, 1103, 1056, 1036, 1024, 1005, 989, 920, 843, 827, 800, 782, 768, 744, 722, 670, 637, 605, 560, 541, 512, 473, 429, 408, 397, 347, 322, 298, 271 and 226 cm$^{-1}$.

D NMR

The 90.56 MHz $^{13}$C CP-MAS NMR spectrum for the Polymorph is shown in FIG. III. Chemical shifts are tabulated in Table I. Data were recorded at ambient temperature and 10 kHz spinning frequency on a Bruker AMX3 60 spectrometer, with 1.6 ms cross polarization, and a repetition time of 15 s. Chemical shifts were externally referenced to the carboxylate signal of a glycine test sample at 176.4 ppm relative to tetramethylsilane, and are regarded as accurate to within +/–0.5 ppm. Peaks were not assigned.

TABLE I $^{13}$C Chemical Shifts of the Polymorph.
Chemical Shift (ppm)

| | | | | |
|---|---|---|---|---|
| 42.2 | 112.3 | 131.5 | 146.5 | 172.4 |
| 50.7 | 113.9 | 134.1 | 151.4 | 177.4 |
| 55.9 | 118.8 | 138.7 | 158.7 | |
| 62.7 | 129.8 | 140.5 | 170.3 | |

E X-Ray Powder Diffraction (XRPD)

The XRPD pattern of the Polymorph is shown below in FIG. IV and a summary of the XRPD angles and calculated lattice spacings characteristic of the Polymorph is given in Table II.

A PW1710 X-ray powder diffractometer (Cu X-ray source) was used to generate the powder pattern using the following acquisition conditions:

| | |
|---|---|
| Tube anode: | Cu |
| Generator tension: | 40 kV |
| Generator current: | 30 mA |
| Start angle: | 3.5 °2θ |
| End angle: | 35.0 °2θ |
| Step size: | 0.020 °2θ |
| Time per step: | 2.3 s |

TABLE II

X-Ray Powder Diffraction Angles and Calculated Lattice Spacings Characteristic of the Polymorph.

| Diffraction Angle (°2θ) | Lattice Spacing (Angstroms) |
|---|---|
| 8.9 | 9.90 |
| 12.0 | 7.35 |
| 14.0 | 6.32 |
| 15.4 | 5.73 |
| 15.9 | 5.55 |
| 16.8 | 5.26 |
| 17.4 | 5.08 |

TABLE II-continued

X-Ray Powder Diffraction Angles and Calculated Lattice
Spacings Characteristic of the Polymorph.

| Diffraction Angle (°2θ) | Lattice Spacing (Angstroms) |
|---|---|
| 18.1 | 4.89 |
| 19.2 | 4.60 |
| 19.6 | 4.52 |
| 20.0 | 4.44 |
| 20.3 | 4.37 |
| 20.8 | 4.27 |
| 21.2 | 4.18 |
| 22.3 | 3.97 |
| 23.7 | 3.80 |
| 24.3 | 3.75 |
| 25.1 | 3.54 |
| 25.8 | 3.44 |
| 26.7 | 3.33 |
| 27.2 | 3.27 |
| 28.7 | 3.10 |
| 29.6 | 3.01 |
| 30.6 | 2.92 |
| 31.6 | 2.83 |
| 32.2 | 2.78 |
| 33.3 | 2.69 |

What is claimed is:

1. A compound which is a polymorphic form of 5-[4-[2-(N-methyl-N-(2-pyridyl)amino)ethoxy]benzyl]thiazolidine-2,4-dione, maleic acid salt, wherein the compound provides at least one of:

(i) an infra red spectrum containing peaks at 1360, 1326, 1241, 714 and 669 $cm^{-1}$;

(ii) a Raman spectrum containing peaks at 1581, 768, 670, 271 and 226 $cm^{-1}$;

(iii) a solid-state $^{13}C$ nuclear magnetic resonance spectrum containing peaks at chemical shifts substantially as set out in Table I; and (iv) an X-ray powder diffraction pattern containing peaks substantially as set out in Table II.

2. A compound which is a polymorphic form of 5-[4-[2-(N-methyl-N-(2-pyridyl)amino)ethoxy]benzyl]thiazolidine-2,4-dione, maleic acid salt, wherein the compound provides each of:

(i) an infra red spectrum containing peaks at 1360, 1326, 1241, 714 and 669 $cm^{-1}$;

(ii) a Raman spectrum containing peaks at 1581, 768, 670, 271 and 226 $cm^{-1}$;

(iii) a solid-state $^{13}C$ nuclear magnetic resonance spectrum containing peaks at chemical shifts substantially as set out in Table 1; and (iv) an X-ray powder diffraction pattern containing peaks substantially as set out in Table II.

3. A compound which is a polymorphic form of 5-[4-[2-(N-methyl-N-(2-pyridyl)amino)ethoxy]benzyl]thiazolidine-2,4-dione, maleic acid salt, wherein the compound provides an infra red spectrum containing peaks at 1360, 1326, 1241, 714 and 669 $cm^{-1}$.

4. A compound which is a polymorphic form of 5-[4-[2-(N-methyl-N-(2-pyridyl)amino)ethoxyl]benzyl]thiazolidine-2,4-dione, maleic acid salt, wherein the compound in a mineral oil dispersion provides an infra red spectrum containing peaks at 1360, 1326, 1241, 714 and 669 $cm^{-1}$.

5. A compound which is a polymorphic form of 5-[4-[2-(N-methyl-N-(2-pyridyl)amino)ethoxyl]benzyl]thiazolidine-2,4-dione, maleic acid salt, wherein the compound provides a Raman spectrum containing peaks at 1581, 768, 670, 271 and 226 $cm^{-1}$.

6. A compound which is a polymorphic form of 5-[4-[2-(N-methyl-N-(2-pyridyl)amino)ethoxyl]benzyl]thiazolidine-2,4-dione, maleic acid salt, wherein the compound provides a solid-state $^{13}C$ nuclear magnetic resonance spectrum containing peaks at chemical shifts substantially as set out in Table I.

7. A compound which is a polymorphic form of 5-[4-[2-(N-methyl-N-(2-pyridyl)amino)ethoxyl]benzyl]thiazolidine-2,4-dione, maleic acid salt, wherein the compound provides an X-ray powder diffraction pattern containing peaks substantially as set out in Table II.

8. A compound which is a polymorphic form of 5-[4-[2-(N-methyl-N-(2-pyridyl)amino)ethoxyl]benzyl]thiazolidine-2,4-dione, maleic acid salt, wherein the compound, in a mineral oil dispersion, provides an infra red spectrum substantially in accordance with FIG. 1.

9. A compound which is a polymorphic form of 5-[4-[2-(N-methyl-N-(2-pyridyl)amino)ethoxyl]benzyl]thiazolidine-2,4-dione, maleic acid salt, wherein the compound provides a Raman spectrum substantially in accordance with FIG. 2.

10. A compound which is a polymorphic form of 5-[4-[2-(N-methyl-N-(2-pyridyl)amino)ethoxyl]benzyl]thiazolidine-2,4-dione, maleic acid salt, wherein the compound provides a solid-state nuclear magnetic resonance spectrum substantially in accordance with FIG. 3.

11. A compound which is a polymorphic form of 5-[4-[2-(N-methyl-N-(2-pyridyl)amino)ethoxyl]benzyl]thiazolidine-2,4-dione, maleic acid salt, wherein the compound provides an X-ray powder diffraction pattern substantially in accordance with FIG. 4.

12. A compound according to any one of claims 1-11, in isolated form.

13. A pharmaceutical composition comprising an effective, non-toxic amount of the compound according to any one of claims 1-11 and a pharmaceutically acceptable carrier therefor, wherein the compound in the composition is in crystalline form.

14. A pharmaceutical composition consisting essentially of an effective, non-toxic amount of the compound according to any one of claims 1-11 and a pharmaceutically acceptable carrier therefor, wherein the compound in the composition is in crystalline form.

15. A pharmaceutical composition according to claim 13, wherein the composition is a solid oral composition.

16. A pharmaceutical composition according to claim 13, wherein the composition is a tablet or capsule.

17. A pharmaceutical composition according to claim 14, wherein the composition is a solid oral composition.

18. A pharamceutical composition according to claim 14, wherein the composition is a tablet or capsule.

19. A method for the preparation of a pharmaceutical composition comprising admixing an effective, non-toxis amount of the compound according to any one of claims 1-11 with a pharmaceutically acceptable carrier therefor.

20. A method for the treatment of diabetes mellitus, conditions associated with diabetes mellitus and complications thereof, in a human or non-human mammal which comprises administering an effective, non-toxic, amount of the compound according to any one of claims 1-11 to a human or non-human mammal in need thereof.

21. A method for the treatment of Type II diabetes in a human or non-human mammal which comprises administering an effective, non-toxic, amount of the compound according to any one of claims 1-11 to a human or non-human mammal in need thereof.

22. A process for preparing the compound according to claim 11, comprising:
   (a) heating a slurry of 5-[4-[2-(N-methyl-N-(2-pyridyl)amino)ethoxy]benzyl]thiazolidine-2,4-dione, maleic acid salt in aqueous denatured ethanol containing up to about 2.5% w/v water for an extended period of time, and
   (b) recovering the compound.

23. A process according to claim 22, wherein the aqueous ethanol comprises 2.5% w/v water.

24. A process according to claim 22, wherein the slurry is heated to a temperature in the range of from 35°-60° C.

25. A process according to claim 22, wherein the slurry is heated to a temperature in the range of from 40°-50° C.

26. A process according to claim 22, wherein the slurry is heated to a temperature of 45° C.

27. A process according to any one of claims 22-26, wherein the extended period of time is 65 hours.

28. A process for preparing the compound according to claim 11, comprising:
   (a) mixing 5-[4-[2-(N-methyl-N-(2-pyridyl)amino)ethoxy]benzyl]thiazolidine-2,4-dione, maleic acid salt with denatured ethanol,
   (b) heating the resulting mixture to an elevated temperature, over an extended period of time, and
   (c) recovering the compound.

29. A process according to claim 28, wherein the elevated temperature is 45-47° C and the extended period of time is 65 hours.

30. A process for preparing the compound according to claim 11, comprising:
   (a) seeding a solution of 5-[4-[2-(N-methyl-N-(2-pyridyl)amino)ethoxy]benzyl]thiazolidine-2,4-dione, maleic acid salt in aqueous denatured ethanol containing up to 2.5% w/v water at 55° C with the compound according to claim 11;
   (b) cooling the resulting mixture to a temperature in the range of from 20° C to 25° C; and
   (c) recovering the compound.

31. A process for preparing the compound according to claim 11, comprising:
   (a) seeding a solution of 5-[4-[2-(N-methyl-N-(2-pyridyl)amino)ethoxy]benzyl]thiazolidine-2,4-dione, maleic acid salt in aqueous denatured ethanol containing 0.8 to 2.5% w/v water at 55° C with the compound according to claim 11;
   (b) cooling the resulting mixture to a temperature in the range of from 20° C to 25° C; and
   (c) recovering the compound.

32. A process for converting the compound according to claim 11 into a polymorph of the compound, comprising:
   (a) preparing a solution of the compound according to claim 11 in a mixture of absolute ethanol and methanol at an elevated temperature;
   (b) cooling the resulting solution to a temperature in the range of from 20° C to 25° C; and
   (c) recovering the polymorph.

33. A process according to claim 32, wherein the elevated temperature is a temperature in the range of from 60°-75° C.

34. A process according to claim 33, wherein the mixture of ethanol and methanol comprises 1% methanol.

35. A process according to claim 34, wherein the elevated temperature is 68° C.

36. A process according to claim 33, further comprising seeding the solution of step (b) with the polymorph of the compound.

37. A process according to claim 33, further comprising filtering the solution formed in step (a).

38. A process according to claim 37, further comprising heating the filtered solution.

39. A process according to claim 38, wherein the filtered solution is first heated to a temperature of 65° C.

40. A process according to claim 39, wherein the heated, filtered solution is cooled to a temperature in the range of from 20° C to 25° C.

41. A process according to claim 40, further comprising seeding the cooled solution with the polymorph of the compound.

* * * * *